US012011520B2

(12) United States Patent
Park

(10) Patent No.: US 12,011,520 B2
(45) Date of Patent: Jun. 18, 2024

(54) INDOOR QUARANTINE SYSTEM USING INDIVIDUAL MASK

(71) Applicant: Jae Hyung Park, Seoul (KR)

(72) Inventor: Jae Hyung Park, Seoul (KR)

( * ) Notice: Subject to any disclaimer, the term of this patent is extended or adjusted under 35 U.S.C. 154(b) by 895 days.

(21) Appl. No.: 17/091,086

(22) Filed: Nov. 6, 2020

(65) Prior Publication Data

US 2022/0118147 A1 Apr. 21, 2022

(30) Foreign Application Priority Data

Oct. 15, 2020 (KR) ........................ 10-2020-0133613

(51) Int. Cl.
*A61L 9/20* (2006.01)
*A61L 9/015* (2006.01)

(52) U.S. Cl.
CPC ................. *A61L 9/20* (2013.01); *A61L 9/015* (2013.01)

(58) Field of Classification Search
None
See application file for complete search history.

(56) References Cited

U.S. PATENT DOCUMENTS

2019/0275357 A1* 9/2019 Palmer, Jr. ............. A61B 5/746

FOREIGN PATENT DOCUMENTS

KR 10-2129455 B1 7/2020

* cited by examiner

*Primary Examiner* — Jelitza M Perez
(74) *Attorney, Agent, or Firm* — KORUS Patent, LLC; Seong Il Jeong

(57) ABSTRACT

Proposed is an indoor quarantine system using an individual mask. The indoor quarantine system may include: an indoor headcount checking device including a headcount checking unit configured to check the number of persons who stay in an indoor space and a headcount providing unit configured to provide headcount information checked by the headcount checking unit to mobile terminals of indoor users; and a disinfection mask worn on an indoor user and activating a disinfection function in accordance with a disinfection command based on the indoor headcount information received from the mobile terminal of the indoor user to disinfect harmful substances around the indoor user.

5 Claims, 4 Drawing Sheets

INDOOR QUARANTINE SYSTEM USING INDIVIDUAL MASK

CROSS REFERENCE TO RELATED APPLICATION

The present application claims priority to Korean Patent Application No. 10-2020-0133613, filed Oct. 15, 2020, the entire contents of which is incorporated herein for all purposes by this reference.

BACKGROUND OF THE INVENTION

Field of the Invention

The present disclosure relates to quarantine technology and, more specifically, to an indoor quarantine system using masks worn on each individual.

Description of the Related Art

Due to Coronavirus disease 2019 (COVID-19) spreading worldwide, the importance of complying with individual living quarantine rules is emphasized and wearing a mask is obligatory in all stages of social distancing as a part of quarantining. Furthermore, according to a paper published in Lancet, which is international journal, it is reported that correct mask wearing shows an effect of decreasing the infection risk by 85% or more. In other words, mask wearing is necessary to lower an infection risk rate of individuals. In particular, it is important to wear a mask indoors, because the infection risk rate is significantly higher indoors than outdoors while it is reported that the infection risk is low outdoors even though people do not wear a mask when a distance of more than 2 meters can be maintained.

RELATED ART DOCUMENTS

Patent Documents

Patent Document 1: Korean Patent No. 10-2129455 (published on Jul. 2, 2020)

SUMMARY OF THE INVENTION

Since there is a high infection risk rate indoors, no matter how well individuals wear protective masks, they will be exposed to the infection risk to a certain extent. Accordingly, the objective of the present disclosure is to provide a technical method capable of further lowering the infection risk rate of persons staying indoors through a new means except for a filter function of a mask.

According to an embodiment of the present disclosure, the indoor quarantine system using an individual mask may include: an indoor headcount checking device including a headcount checking unit configured to check the number of persons who stay in an indoor space and a headcount providing unit providing headcount information checked by the headcount checking unit to mobile terminals of indoor users; and a disinfection mask worn on the indoor user and activating a disinfection function in accordance with a disinfection command based on the indoor headcount information received from the mobile terminal of the indoor user to disinfect harmful substances around the indoor user.

The headcount checking unit may use at least one human body sensor disposed in a space for entering and exiting the indoor space to check the number of persons who exist in the indoor space and the headcount information providing unit may broadcast the indoor headcount information through a Bluetooth beacon to allow the mobile terminal of the indoor users to receive the indoor headcount information.

The disinfection mask may include: an ozone generator disposed at the outside of the mask to generate ozone to the outside; and an ultraviolet ray generator disposed at the inside of the mask to generate ultraviolet (UV) rays to the inside.

The indoor quarantine system may further include a disinfection application executed in the mobile terminal of each indoor user and controlling activation or deactivation of a disinfection function of the disinfection mask in accordance with the indoor headcount information received from the indoor headcount checking device, wherein the disinfection application can variably control an ultraviolet ray generation strength and an ozone generation strength in accordance with the indoor headcount information when the activation is controlled.

The disinfection mask may further include a power supply unit charging a battery of the mask with electric energy induced through a solenoid coil disposed on a bottom surface or a solenoid coil disposed in shoes of the indoor user, or electric energy induced through a piezoelectric device installed in shoes of the indoor user.

The present disclosure utilizes a disinfection mask worn on each individual to perform proper disinfection/quarantine in an indoor space, such as a bus, a subway, and the like as well as a school and an academy, thereby providing effect of preventing droplet infection among persons.

DETAILED DESCRIPTION OF THE INVENTION

The foregoing and further aspects of the present disclosure will become more apparent through the preferred embodiments described with reference to the accompanying drawings. Hereinafter, the present disclosure will be described in detail to enable those skilled in the art to easily understand and reproduce the present disclosure through the embodiments of the present disclosure.

Figure 1:
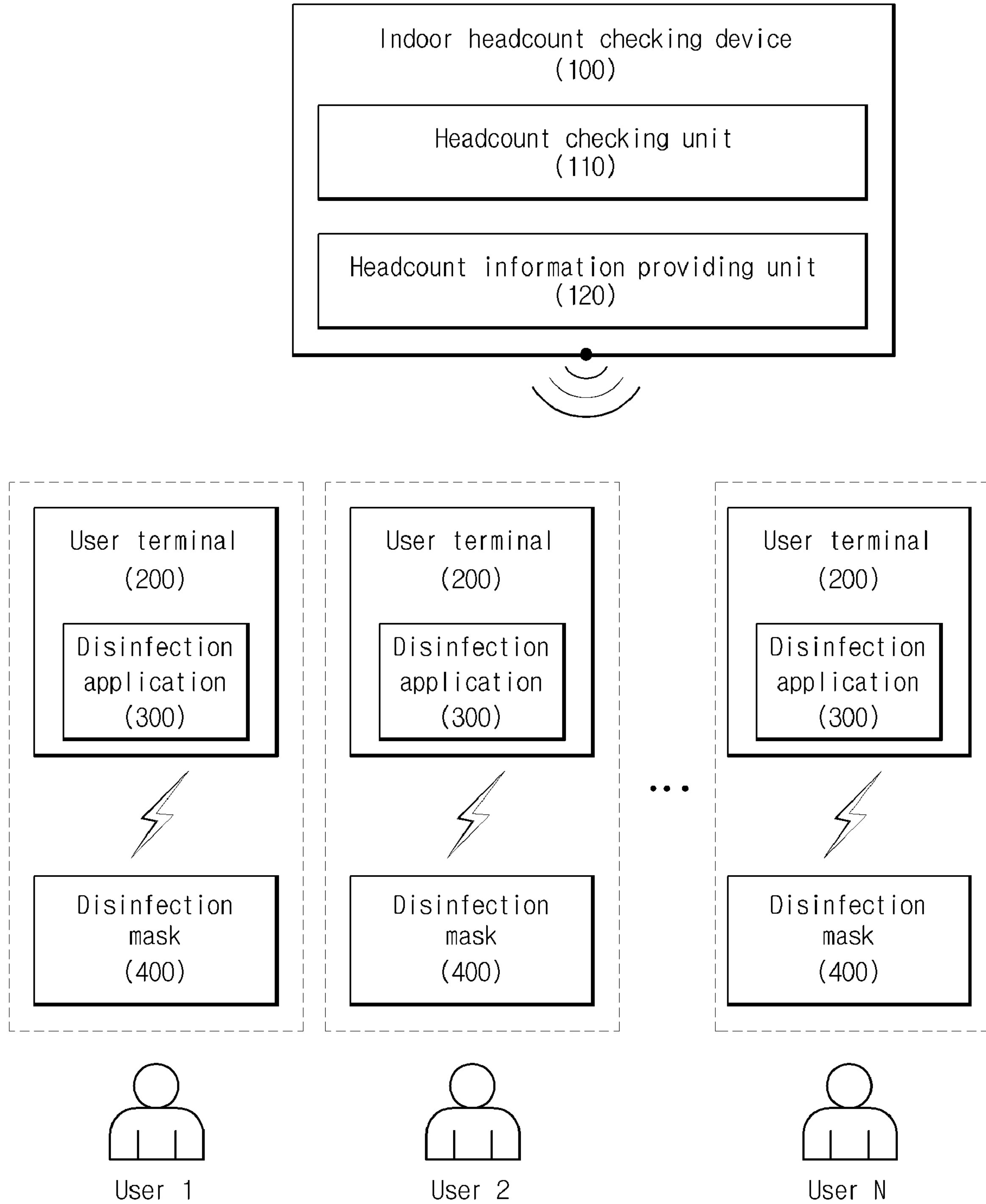
FIG. 1 is a block diagram of an individual quarantine system according to an embodiment of the present disclosure.
Figure 2:
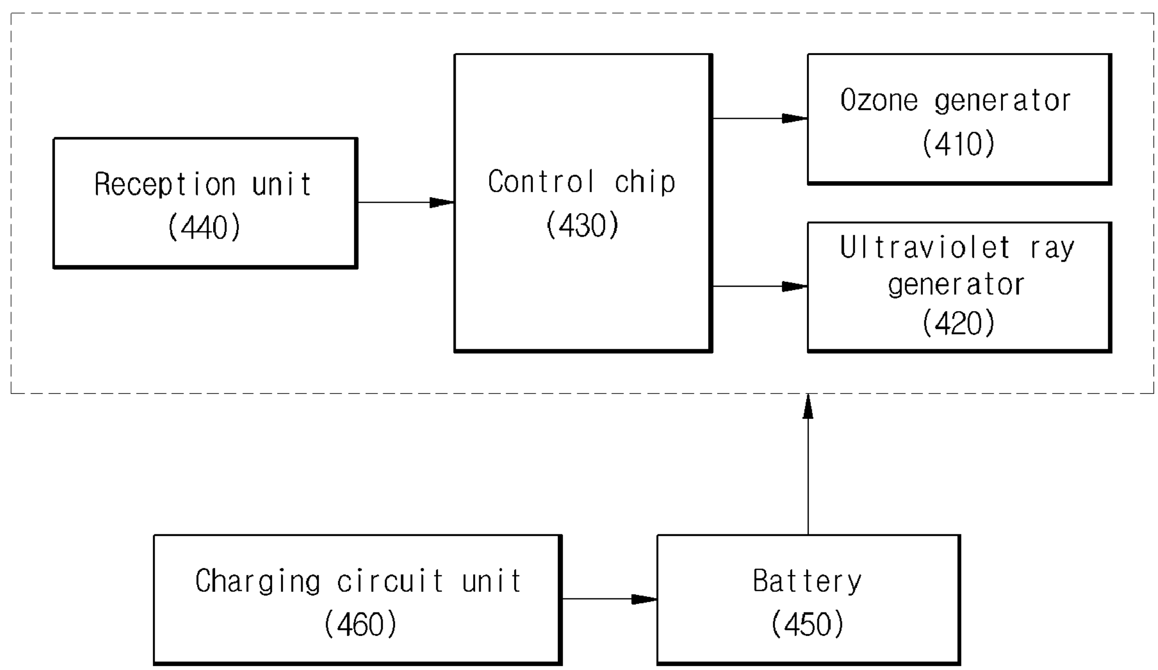
FIG. 2 is a block diagram of a disinfection mask according to an embodiment of the present disclosure.

FIG. 1 is a block diagram of an individual quarantine system according to an embodiment of the present disclosure. The indoor headcount checking device 100, which counts the number of persons who stay in an indoor space, such as a public facility, an office, a classroom, a restaurant, a bus/subway, and the like, to inform indoor users of a headcount, may include the headcount checking unit 110 and the headcount information providing unit 120. The headcount checking unit 110 counts a total number of persons who stay in the indoor space. According to the embodiment of the present disclosure, the headcount checking unit 110 detects the users, who enter and exit the indoor space, through the human body sensor disposed at a gate for entering and exiting the indoor space to check the total number of persons who remain in the indoor space. At this time, the human body sensor used for detecting the users who enter and exit the indoor space may be an infrared sensor, an ultraviolet sensor, and the like.

Figure 3:
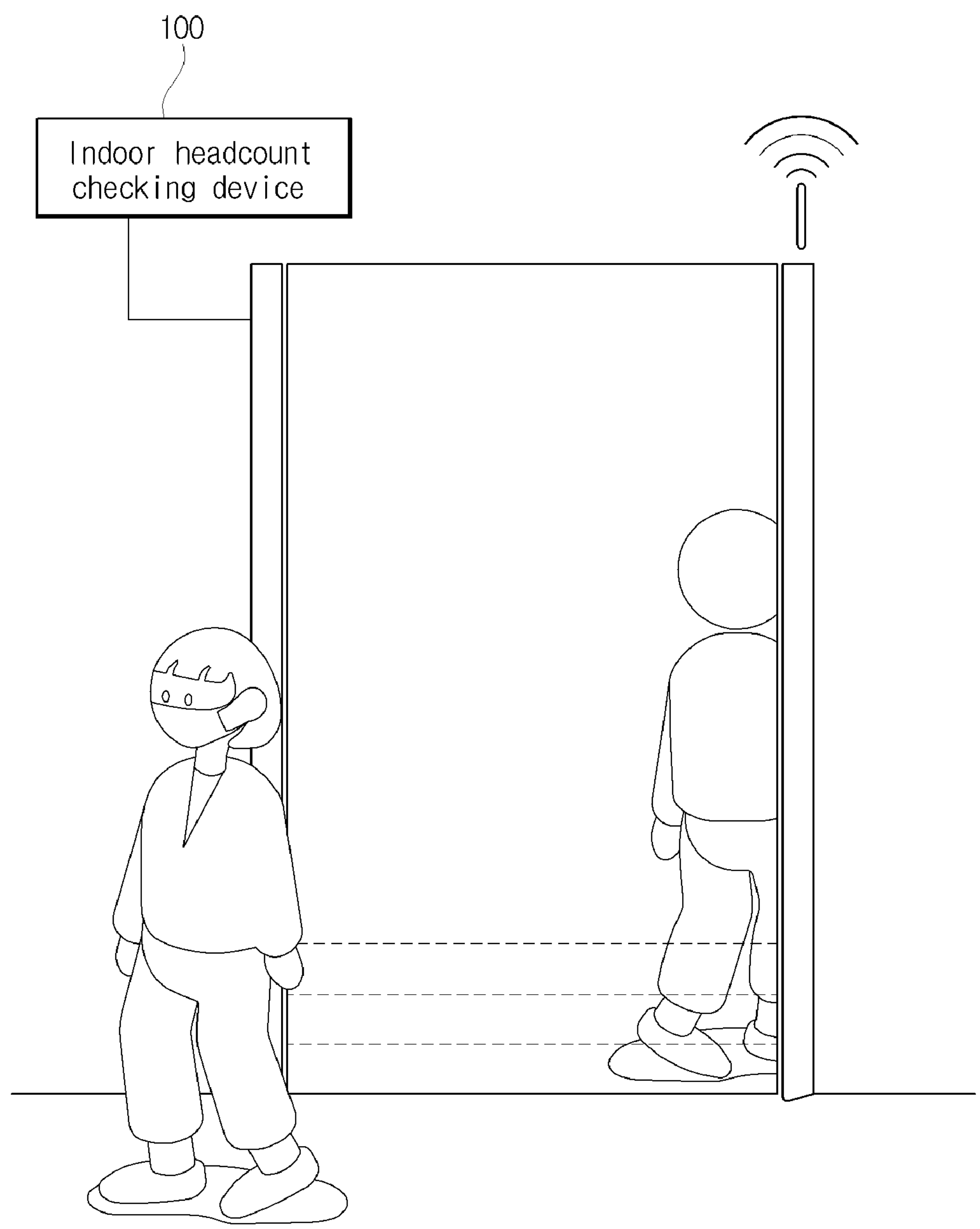
FIG. 3 is a view illustrating the counting the number of persons who passes through an indoor gate.

The headcount information providing unit 120 transmits headcount information checked by the headcount checking unit 110 to user terminals 200 through wireless communications. According to the embodiment of the present disclosure, since the headcount information providing unit 120 broadcasts a signal including the headcount information to the indoor space through a short-range communication means, such as a Bluetooth beacon and the like, the user terminal 200 staying indoors can receive the signal. As shown in FIG. 3, the headcount checking unit 110 can count the users who enter and exit through the gate and can wirelessly transmit the indoor headcount information acquired therethrough to the indoor space.

Each user terminal 200 is a communicable computing terminal held by the user, i.e., a smartphone. An application 300 (hereinafter, referred to as a "quarantine application") for providing a quarantine service using an individual mask is installed and executed in the user terminal 200. The quarantine application 300 receives the headcount information transmitted from the indoor headcount checking device 100 and activates the disinfection function included in the disinfection mask 400 worn on the user or deactivates the activated disinfection function in accordance with the headcount information transmitted from the indoor headcount checking device 100. To control the activation or deactivation of the disinfection function, the quarantine application 300 can use a short-range wireless communication resource of the user terminal 200, i.e., Bluetooth. In other words, a wireless channel can be formed between the user terminal 200 and the user's disinfection mask 400 through Bluetooth pairing and the user terminal 200 can control the disinfection function of the disinfection mask 400 through wireless communications.

Each disinfection mask 400 includes the disinfection function except for a fine particle prevention function using a filter. According to the embodiment of the present disclosure, the disinfection mask 400 includes the ozone generator 410 and the ultraviolet ray generator 420. The ozone generator 410 is disposed at the outside of the disinfection mask 400 to generate ozone to the outside of the mask and the ultraviolet ray generator 420 is disposed at the inside of the disinfection mask 400 to generate ultraviolet rays to the inside of the mask to disinfect harmful substances around the user. In other words, since the inside and the outside of the mask are disinfected in real time, propagation of bacteria and viruses among persons is blocked. A control chip 430, which is a configuration to control the ozone generator 410 and the ultraviolet ray generator 420, activates or deactivates the disinfection function in accordance with a disinfection control command that is wirelessly received from the disinfection application 300 through a reception unit 440. In other words, the control chip 430 activates the ozone generator 410 and the ultraviolet ray generator 420 when receiving a disinfection start command, and deactivates the ozone generator 410 and the ultraviolet ray generator 420 when receiving a disinfection end command.

Figure 4:
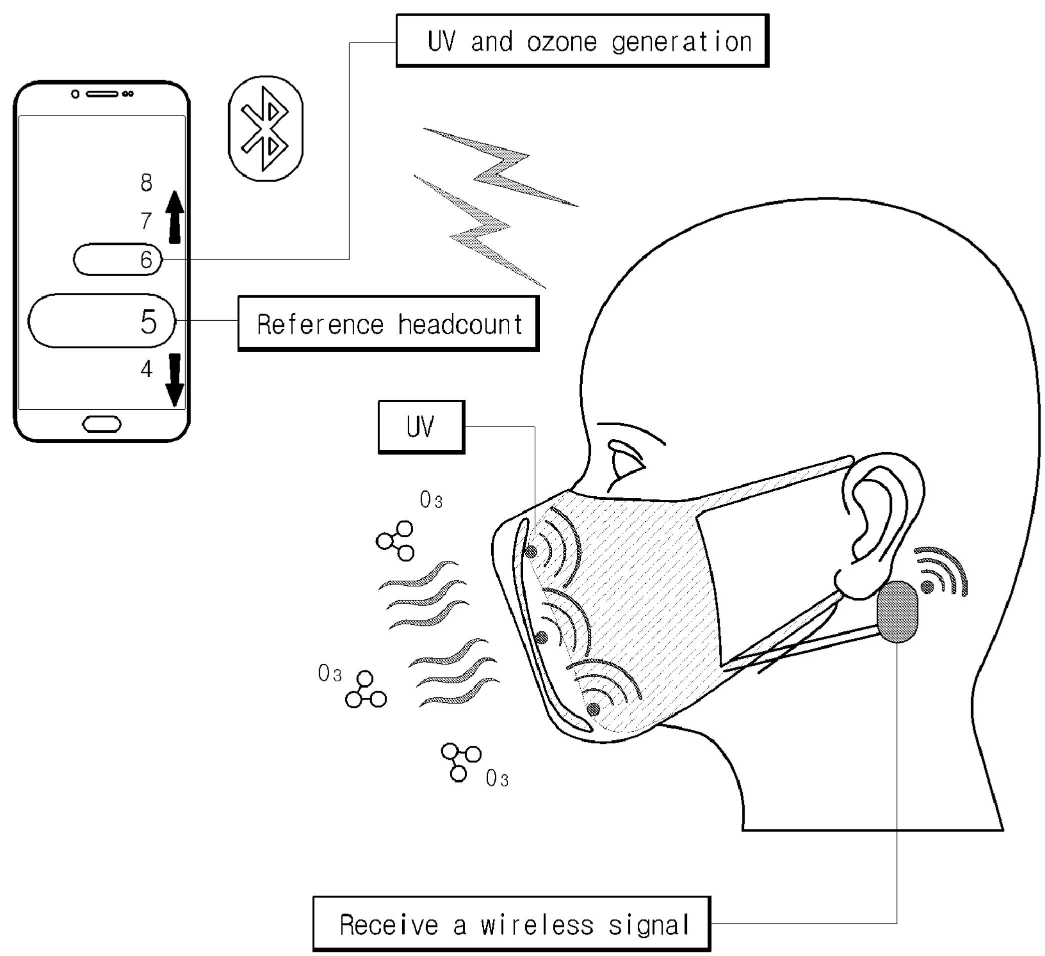
FIG. 4 is a view illustrating ozone and ultraviolet ray generation of a disinfection mask according to control of a smartphone.

In only the case in which an indoor headcount exceeds a reference headcount, the disinfection application 300 activates the disinfection function of the disinfection mask 400. At this time, the reference headcount can be set different from each indoor space and can be set based on a predetermined area. In addition, in the case of activating the disinfection function of the disinfection mask 400 since the indoor headcount exceeds the reference headcount, the disinfection application 300 can vary the amount of ozone and the amount of ultraviolet rays in accordance with the number of persons. To this end, information on the ozone generation strength and the ultraviolet ray generation strength required for each indoor headcount can be previously stored in a database and the disinfection application 300 can set the amount of ozone and the amount of ultraviolet rays checked through the database to activate the disinfection function. Accordingly, the control chip 430 adjusts and controls an ozone generation level of the ozone generator 410 and an ultraviolet ray generation level of the ultraviolet ray generator 410 in accordance with the amount of ozone and the amount of ultraviolet rays set by the disinfection application 300. In relation to this, FIG. 4 illustrates that the disinfection mask 400 generates ozone and ultraviolet rays in accordance with the indoor headcount, wherein as the indoor headcount increases, the ozone generation strength and the UV generation strength increase.

In addition, the battery 450 of the disinfection mask 400 can be charged with electricity supplied from the outside by a charging circuit unit 460. The charging circuit unit 460 can charge the battery 450 with electric energy supplied from external commercial electricity or can also charge the battery 450 with electric energy acquired through a solar cell panel. Moreover, the charging circuit unit 460 can charge the battery 450 with electric energy acquired from a piezoelectric device installed in the user's shoes or can charge the battery 450 with electric energy induced through the solenoid coil disposed on a bottom surface of the indoor space and the like or the solenoid coil disposed in the user's shoes.

On the other hand, the indoor headcount checking device 100 can report indoor headcount to a control server (not shown) in real time. Accordingly, the control server can check the indoor headcount and can transfer the indoor headcount information to the disinfection applications 300 of the users who stay in the indoor space. In other words, the disinfection function of the disinfection mask 400 can be controlled through the control server.

So far I looked at the center of the preferred embodiment for the present disclosure. Those skilled in the art will appreciate that the present disclosure can be implemented in a modified form without departing from the essential features of the present disclosure. Therefore, the disclosed embodiments should be considered in descriptive sense only and not for purposes of limitation. The scope of the present disclosure is shown in the claims rather than the foregoing description, and all differences within the scope will be construed as being included in the present disclosure.

What is claimed is:

1. An indoor quarantine system using an individual mask, the system comprising:

an indoor headcount checking device including a headcount checking unit configured to check the number of persons who stay in an indoor space and a headcount information providing unit configured to provide indoor headcount information checked by the headcount checking unit to mobile terminals of indoor users; and a disinfection mask worn on an indoor user and activating a disinfection function in accordance with a disinfection command based on the indoor headcount information received from the mobile terminal of the indoor user to disinfect harmful substances around the indoor user.

2. The system of claim 1, wherein the headcount checking unit uses at least one human body sensor disposed in a space for entering and exiting the indoor space to check the number of persons who exist in the indoor space, and the headcount information providing unit broadcasts the indoor headcount information through a Bluetooth™ beacon to allow the mobile terminals of the indoor users to receive the indoor headcount information.

3. The system of claim 1, wherein the disinfection mask comprises:

an ozone generator disposed at the outside of the mask to generate ozone to the outside of the mask; and an ultraviolet ray generator disposed at the inside of the mask to generate ultraviolet (UV) rays to the inside of the mask.

4. The system of claim 3, further comprising:

a disinfection application executed in the mobile terminal of each indoor user to control activation or deactivation of a disinfection function of the disinfection mask in accordance with the indoor headcount information received from the indoor headcount checking device, wherein the disinfection application variably controls an ultraviolet ray generation strength and an ozone generation strength in accordance with the indoor headcount information when the activation is controlled.

5. The system of claim 3, wherein the disinfection mask further comprises:

a power supply unit charging a battery of the mask with electric energy induced through a solenoid coil disposed on a bottom surface or a solenoid coil disposed in shoes of the indoor user, or electric energy induced through a piezoelectric device installed in shoes of the indoor user.

* * * * *